(12) United States Patent
Weibel et al.

(10) Patent No.: US 9,849,099 B2
(45) Date of Patent: Dec. 26, 2017

(54) ANTIMICROBIAL COMPOUNDS, COMPOSITIONS AND METHODS OF USE THEREOF

(71) Applicant: WISCONSIN ALUMNI RESEARCH FOUNDATION, Madison, WI (US)

(72) Inventors: Douglas Benjamin Weibel, Madison, WI (US); Katherine Ann Hurley, Madison, WI (US); Katherine Cassidy Faulkner, Boxborough, MA (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 0 days.

(21) Appl. No.: 15/233,450

(22) Filed: Aug. 10, 2016

(65) Prior Publication Data

US 2016/0374964 A1    Dec. 29, 2016

Related U.S. Application Data

(63) Continuation of application No. 14/790,380, filed on Jul. 2, 2015, now Pat. No. 9,440,920.

(60) Provisional application No. 62/020,490, filed on Jul. 3, 2014.

(51) Int. Cl.
| | | |
|---|---|---|
| *A61K 31/137* | (2006.01) | |
| *A01N 33/10* | (2006.01) | |
| *C07D 209/16* | (2006.01) | |
| *A61K 31/4045* | (2006.01) | |
| *A01N 43/38* | (2006.01) | |

(52) U.S. Cl.
CPC ............ *A61K 31/137* (2013.01); *A01N 33/10* (2013.01); *A01N 43/38* (2013.01); *A61K 31/4045* (2013.01); *C07D 209/16* (2013.01)

(58) Field of Classification Search
CPC .. A61K 31/137; A61K 31/4045; A01N 33/10; A01N 43/38; C07D 209/16
USPC ....................................................... 514/415
See application file for complete search history.

(56) References Cited

U.S. PATENT DOCUMENTS

| | | | | |
|---|---|---|---|---|
| 5,773,469 A | * | 6/1998 | Kanojia | ............... A61K 31/137 514/480 |
| 2016/0002163 A1 | | 1/2016 | Weibel et al. | |

FOREIGN PATENT DOCUMENTS

| | | |
|---|---|---|
| WO | 2004062674 A2 | 7/2004 |
| WO | 2005007162 A1 | 1/2005 |
| WO | 2008141012 A2 | 11/2008 |
| WO | 2010054102 A2 | 5/2010 |
| WO | 2011075136 A1 | 6/2011 |

OTHER PUBLICATIONS

Glennon et al.; "Binding of O-Alkyl Derivatives of Serotonin at Human 5-HT1DB Receptors"; J. Med. Chem. 39; pp. 314-322; (1996).
Glennon, et al.; "5-(Nonyloxy)tryptamine: A Novel High-Affinity 5-HT1DB Serotonin Receptor Agonist"; J. Med. Chem; 37; pp. 2828-2830; (1994).
Hsieh et al.; "The Activation of Pheripheral 5-HT1A Receptors Can Inhibit Seminal Vesicle Contraction: An In Vivo Animal Study"; Urology; 78(2); pp. 376-379 (2011).
Methods for Dilution Antimicrobial Susceptibility Tests for Bacteria That Grow Aerobically; Approved Standard Eighth Edition; Clinical and Laboratory Standards Institute: Wayne PA; 10 pages; (2006 ).
Oyamada et al.; "Anucleate Cell Blue Assay: a Useful Tool for Identifying Novel Type II Topoisomerase Inhibitors"; Antimicrobial Agents and Chemotherapy; pp. 348-350; (2006).
Pankey et al.; "Clinical Relevance of Bacteriostatic Versus Bactericidal Mechanisms of Action in the Treatment of Gram-Positive Bacterial Infections"; in Clini. Infect. Dis.; 38; pp. 864-870; (2004).
Wachi et al.; Irregular Nuclear Localization and Anucleate Cell Production in *Escherichia coli* Induced by a Ca2+ Chelator, EGTA.

* cited by examiner

*Primary Examiner* — Yevegeny Valenrod
(74) *Attorney, Agent, or Firm* — Cantor Colburn LLP

(57) ABSTRACT

Described herein are antimicrobial compounds identified via a high-throughput screen to identify compounds that produce anucleate cells in *E. coli* after cell division occurs. Compound 1 (5-nonyloxytryptamine) and its analogs are small molecule inhibitors of the nucleoid occlusion system and/or proteins that are responsible for maintaining the structure of the chromosome. The antimicrobial compounds are useful to treat bacterial infections as well as to inhibit bacterial growth.

18 Claims, 1 Drawing Sheet

ANTIMICROBIAL COMPOUNDS, COMPOSITIONS AND METHODS OF USE THEREOF

CROSS-REFERENCE TO RELATED APPLICATIONS

This application is a continuation of U.S. application Ser. No. 14/790,380, filed on Jul. 2, 2015, which claims priority to U.S. Provisional Application 62/020,490 filed on Jul. 3, 2014, which is incorporated herein by reference in its entirety.

STATEMENT REGARDING FEDERALLY SPONSORED RESEARCH & DEVELOPMENT

This invention was made with government support under OD008735 awarded by the National Institutes of Health. The government has certain rights in the invention.

FIELD OF THE DISCLOSURE

The present disclosure is related to broad-spectrum antimicrobial compounds, pharmaceutical compositions comprising the antimicrobial compounds, and methods of treating bacterial infections with the antimicrobial compounds.

BACKGROUND

While the prevalence of multi-drug resistant pathogens continues to rise, the rate at which new clinical antimicrobials are introduced has declined significantly. In addition, the treatment of persistent infections has been complicated by pathogen phenotypes. Bacteria that grow very slowly are often associated with prolonged infections, and they are particularly tolerant to many of the clinically important classes of antibiotics that inhibit rapidly growing cells. For example, the β-lactam family of antibiotics inhibits enzymes involved in the synthesis of peptidoglycan, and is thus most effective at targeting microbes that grow rapidly and continuously synthesize new cell wall. Relying on antibiotics that require fast metabolism and growth creates long-term problems, because dormant bacteria, as well as those associated with biofilms and other multicellular structures, may survive antibiotic treatments, become predisposed to developing drug resistance, and cause a relapse.

Previously, an assay was developed to detect specific inhibitors of chromosome portioning in *Escherichia coli*. (Oyamada et al., "Anucleate Cell Blue Assay: A Useful Tool for Identifying Novel Type II Topoisomerase Inhibitors," Antimicrobial Agents and Chemotherapy, 50, pp. 348-350, (2006)). In the so-called anucleate cell blue assay, detection of anucleate cell production is used to screen for specific inhibitors of chromosome portioning. Compounds that inhibit either DNA gyrase or topoisomerase IV in vitro were identified and the antibacterial activity against certain drug-resistant *Staphylococcus aureus* strains was measured. The anucleate cell blue assay thus appears to be a useful tool for identifying potential antibiotics.

What are needed are new broad-spectrum antimicrobial compounds, particularly antimicrobial compounds that inhibit chromosome segregation during cell division and/or inhibit proteins responsible for maintaining the structure of the chromosome.

BRIEF SUMMARY

In one aspect, included herein is an antimicrobial compound selected from

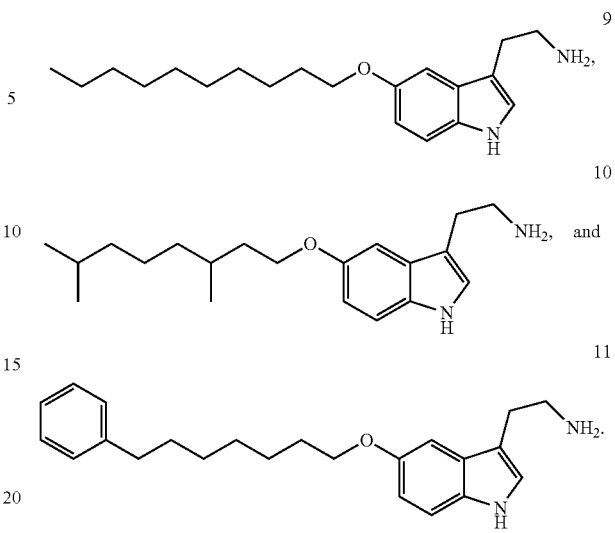

Also included are pharmaceutical compositions including the compounds and a pharmaceutically acceptable excipient.

Further included herein is an antimicrobial compound of Formula I, or a pharmaceutically acceptable salt thereof, as well as methods of treating a subject in need of treatment for a bacterial infection and methods of inhibiting bacterial growth with the compounds,

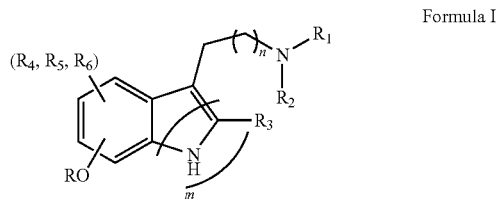

Formula I wherein

R is a substituted or unsubstituted $C_5$-$C_{18}$ alkyl group, a substituted or unsubstituted $C_5$-$C_{18}$ alkenyl group, a substituted or unsubstituted $C_5$-$C_{18}$ alkynyl group, a substituted or unsubstituted $C_5$-$C_{18}$ cycloalkyl group, a substituted or unsubstituted $C_6$-$C_{18}$ cycloalkenyl group, a substituted or unsubstituted $C_8$-$C_{18}$ cycloalkynyl group, a substituted or unsubstituted $C_5$-$C_{18}$ heteroalkyl group, a substituted or unsubstituted $C_5$-$C_{18}$ heterocycloalkyl group, a substituted or unsubstituted $C_7$-$C_{30}$ arylalkyl group, a substituted or unsubstituted $C_7$-$C_{30}$ aryloxyalkyl group, or a substituted or unsubstituted $C_7$-$C_{30}$ arylthioalkyl group;

$R_1$ and $R_2$ are each independently hydrogen, a substituted or unsubstituted $C_1$-$C_{18}$ alkyl group, a substituted or unsubstituted $C_3$-$C_{18}$ cycloalkyl group, a substituted or unsubstituted $C_6$-$C_{20}$ aryl group, or a substituted or unsubstituted $C_7$-$C_{30}$ arylalkyl group;

$R_3$, $R_4$, $R_5$, and $R_6$ are each independently hydrogen, a halogen, a cyano group, a nitrile group, a sulfonate group, an amine group, a substituted or unsubstituted $C_1$-$C_{18}$ alkyl group, a substituted or unsubstituted $C_1$-$C_{18}$ alkoxy group, a substituted or unsubstituted $C_1$-$C_{18}$ alkylthio group, a substituted or unsubstituted $C_3$-$C_{18}$ cycloalkyl group, a substituted or unsubstituted $C_3$-$C_{18}$ cycloalkoxy group, a substituted or unsubstituted $C_3$-$C_{18}$ cycloalkylthio group, a substituted or unsubstituted $C_6$-$C_{20}$ aryl group; a substituted or unsubstituted $C_6$-$C_{20}$ aryloxy group, a substituted or unsubstituted $C_6$-$C_{20}$ arylthio group, or a substituted or unsubstituted $C_7$-$C_{30}$ arylalkyl group;

m is 0 or 1; and n is an integer of 1 to 5.

Further included herein is an antimicrobial compound of Formula II, Formula III, Formula IV, or a pharmaceutically acceptable salt thereof, as well as methods of treating a subject in need of treatment for a bacterial infection and methods of inhibiting bacterial growth with the compounds,

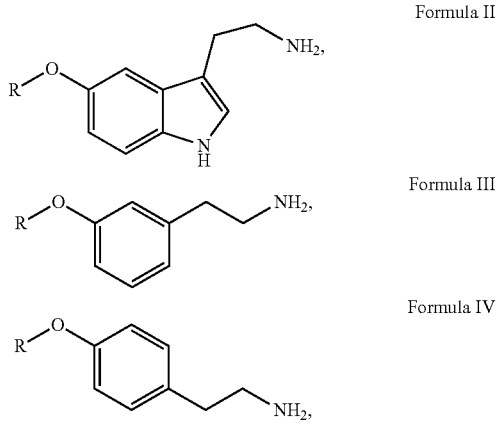

Formula II

Formula III

Formula IV wherein R is a substituted or unsubstituted $C_5$-$C_{18}$ alkyl group, a substituted or unsubstituted $C_5$-$C_{18}$ alkenyl group, a substituted or unsubstituted $C_5$-$C_{18}$ alkynyl group, a substituted or unsubstituted $C_5$-$C_{18}$ cycloalkyl group, a substituted or unsubstituted $C_6$-$C_{18}$ cycloalkenyl group, a substituted or unsubstituted $C_8$-$C_{18}$ cycloalkynyl group, a substituted or unsubstituted $C_5$-$C_{18}$ heteroalkyl group, a substituted or unsubstituted $C_5$-$C_{18}$ heterocycloalkyl group, a substituted or unsubstituted $C_7$-$C_{30}$ arylalkyl group, a substituted or unsubstituted $C_7$-$C_{30}$ aryloxyalkyl group, or a substituted or unsubstituted $C_7$-$C_{30}$ arylthioalkyl group. Also included are methods of treating bacterial infections and methods of inhibiting bacterial growth with the compounds of Formula I.

Figure 1A:
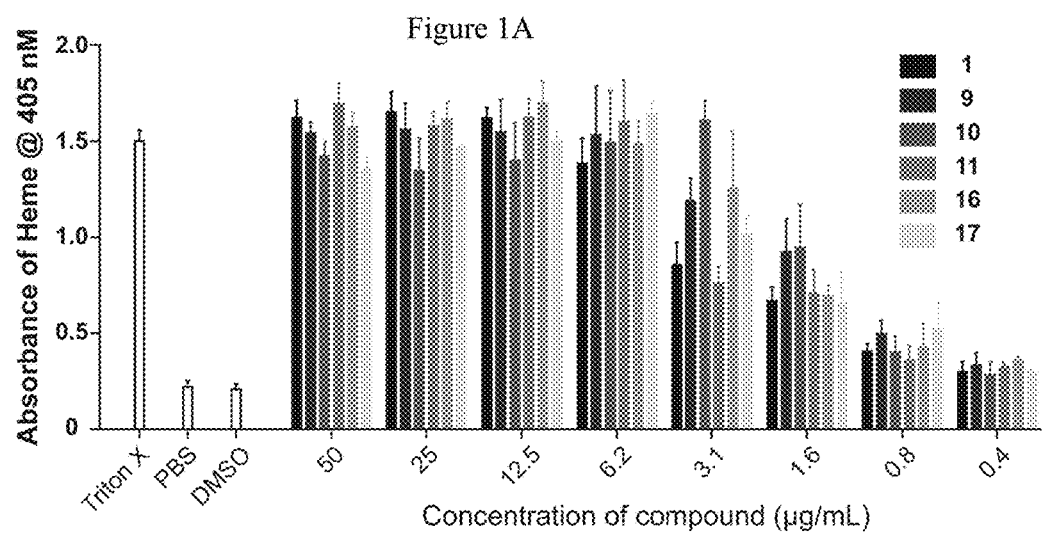
FIGS. 1A and B show Rabbit RBC hemolysis assays performed at various concentrations above and below the MIC of 1 against *E. coli* BW25113 (MIC=6.2 μg/mL). 0.25% Triton-X is a positive control, Phosphate buffered saline (PBS) is a negative control and 1% DMSO is a solvent control. Columns represent means and errors bars represent standard deviations of 3 replicates. A) The absorbance of heme (lysed RBCs) after 6 hours of incubation at 37° C. B) The absorbance of heme (lysed RBCs) after 17 hours of incubation at 37° C.
Figure 1B:
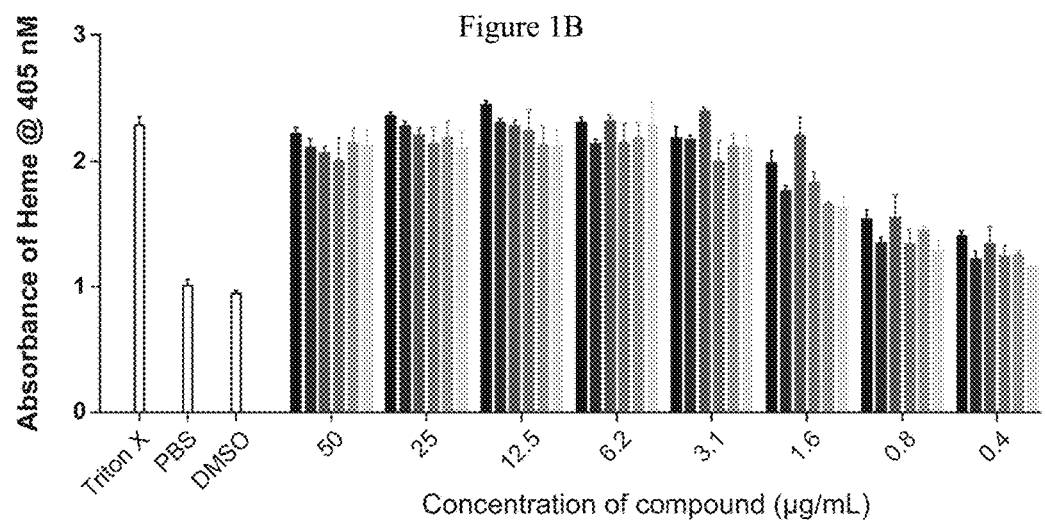

The above-described and other features will be appreciated and understood by those skilled in the art from the following detailed description, and appended claims.

DETAILED DESCRIPTION

The inventors of the present application developed a high-throughput assay and screened small molecule libraries to identify compounds that produce anucleate cells of the model bacterium *Escherichia coli* after division occurs (i.e., cells that lack a copy of the chromosome), which prevents replication. The goal was to identify small molecule inhibitors of the nucleoid occlusion system (which synchronizes chromosome segregation between the mother and daughter cell and cell division) and/or proteins that are responsible for maintaining the structure of the chromosome (i.e., structural maintenance of chromosome proteins).

Specifically, a screen of small molecule libraries identified 5-nonyloxytryptamine (Compound 1, Table 1) as a potent hit in this screen; this compound has been reported as an anticancer drug and is currently under evaluation in animal studies for its anti-cancer activity. Antibiotic activity of Compound 1 does not appear to have been reported previously. To confirm the activity of Compound 1, the compound was synthesized and the minimum inhibitory concentration (MIC) and minimum bacterial concentration (MBC) were determined against a broad panel of human pathogens. As shown herein, Compound 1 has an MIC of 5-20 μM against several pathogens; the only exception was *Pseudomonas aeruginosa* for which Compound 1 has an MIC of 80 μM, which is consistent with the challenges of drug efflux in this organism. Compound 1 has broad-spectrum activity against Gram-positive and Gram-negative bacteria; in some organisms Compound 1 has bacteriostatic activity and in others Compound 1 is bactericidal.

Several analogs of Compound 1 (Compounds 7-12, Table 1) in which the alkyl group at the 5-hydroxy position of tryptamine was varied were synthesized and tested. Several structurally related compounds (Compounds 2-6, Table 1) were also tested against the panel of pathogens. The O-alkoxytryptamine analogs (Compounds 7-11, Table 1) are differentiated from other tryptamines (Compounds 2-6, Table 1) to demonstrate that the activity of compounds 1 and 7-11 is unique to the O-alkoxytryptamine family of compounds. Compounds 2-6 were largely ineffective as antibiotics (See Examples). Of the compounds synthesized and tested, at least Compounds 8, 10, 11 and 12 appear to be novel compounds. Compounds 9, 10 and 11 displayed MICs that are either the same or 2-fold different from 1, thereby suggesting that these compounds share the same potency.

TABLE 1

Compound 1 and analogs

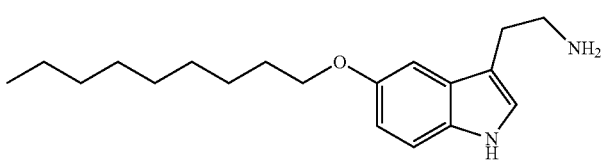 [SMILES: CCCCCCCCCOc1ccc2[nH]cc(CCN)c2c1]

1

TABLE 1-continued
Compound 1 and analogs
| | |
|---|---|
| 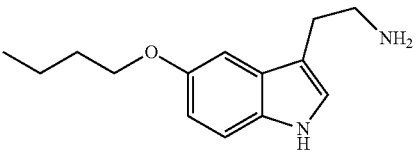 [SMILES: CCCCOc1ccc2[nH]cc(CCN)c2c1] | 7 |
| 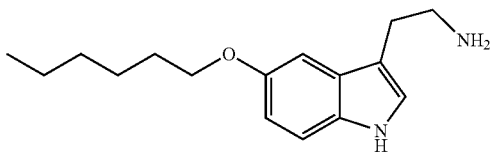 [SMILES: CCCCCCOc1ccc2[nH]cc(CCN)c2c1] | 8 |
| 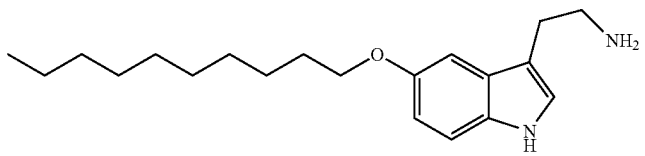 [SMILES: CCCCCCCCCCOc1ccc2[nH]cc(CCN)c2c1] | 9 |
| 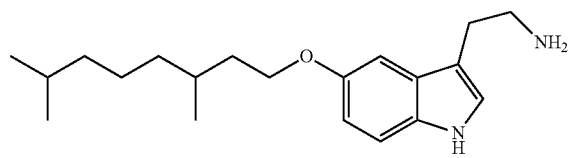 [SMILES: CC(C)CCCC(C)CCOc1ccc2[nH]cc(CCN)c2c1] | 10 |
| 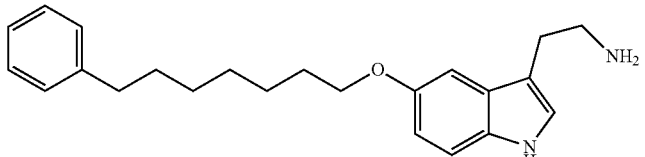 | 11 |
| 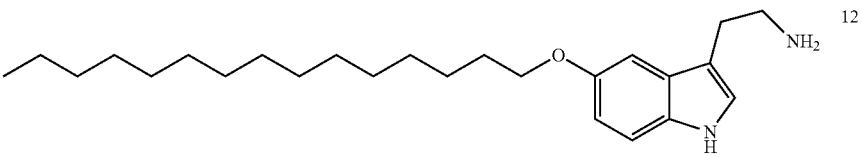 | 12 |
| 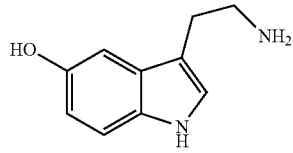 [SMILES: NCCc1c[nH]c2ccc(O)cc12] | 2 |
| 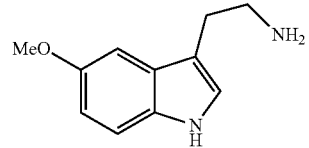 [SMILES: COc1ccc2[nH]cc(CCN)c2c1] | 3 |
| 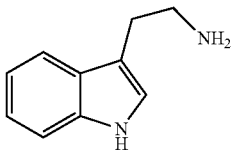 [SMILES: NCCc1c[nH]c2ccccc12] | 4 |

TABLE 1-continued

Compound 1 and analogs

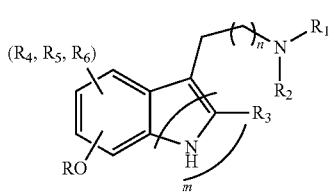

In one aspect, an antimicrobial compound or a pharmaceutically acceptable salt thereof has Formula I:

Formula I wherein
R is a substituted or unsubstituted $C_5$-$C_{18}$ alkyl group, a substituted or unsubstituted $C_5$-$C_{18}$ alkenyl group, a substituted or unsubstituted $C_5$-$C_{18}$ alkynyl group, a substituted or unsubstituted $C_5$-$C_{18}$ cycloalkyl group, a substituted or unsubstituted $C_6$-$C_{18}$ cycloalkenyl group, a substituted or unsubstituted $C_8$-$C_{18}$ cycloalkynyl group, a substituted or unsubstituted $C_5$-$C_{18}$ heteroalkyl group, a substituted or unsubstituted $C_4$-$C_{18}$ heterocycloalkyl group, a substituted or unsubstituted $C_7$-$C_{30}$ arylalkyl group, a substituted or unsubstituted $C_7$-$C_{30}$ aryloxyalkyl group, or a substituted or unsubstituted $C_7$-$C_{30}$ arylthioalkyl group;

$R_1$ and $R_2$ are each independently hydrogen, a substituted or unsubstituted $C_1$-$C_{18}$ alkyl group, a substituted or unsubstituted $C_3$-$C_{18}$ cycloalkyl group, a substituted or unsubstituted $C_6$-$C_{20}$ aryl group, or a substituted or unsubstituted $C_7$-$C_{30}$ arylalkyl group;

$R_3$, $R_4$, $R_5$, and $R_6$ are each independently hydrogen, a halogen, a cyano group, a nitrile group, a sulfonate group, an amine group, a substituted or unsubstituted $C_1$-$C_{18}$ alkyl group, a substituted or unsubstituted $C_1$-$C_{18}$ alkoxy group, a substituted or unsubstituted $C_1$-$C_{18}$ alkylthio group, a substituted or unsubstituted $C_3$-$C_{18}$ cycloalkyl group, a substituted or unsubstituted $C_3$-$C_{18}$ cycloalkoxy group, a substituted or unsubstituted $C_3$-$C_{18}$ cycloalkylthio group, a substituted or unsubstituted $C_6$-$C_{20}$ aryl group; a substituted or unsubstituted $C_6$-$C_{20}$ aryloxy group, a substituted or unsubstituted $C_6$-$C_{20}$ arylthio group, or a substituted or unsubstituted $C_7$-$C_{30}$ arylalkyl group;

m is 0 or 1; and n is an integer of 1 to 5.

In another aspect, an antimicrobial compound has the following Formula II, III, IV or a pharmaceutically acceptable salt thereof,

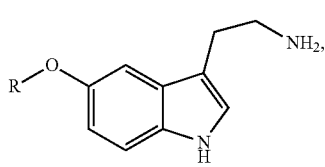
Formula II

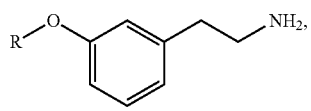
Formula III

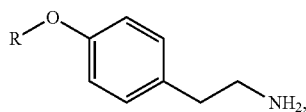
Formula IV wherein R is a substituted or unsubstituted $C_5$-$C_{18}$ alkyl group, a substituted or unsubstituted $C_5$-$C_{18}$ alkenyl group, a substituted or unsubstituted $C_5$-$C_{18}$ alkynyl group, a substituted or unsubstituted $C_4$-$C_{18}$ cycloalkyl group, a substituted or unsubstituted $C_5$-$C_{18}$ cycloalkenyl group, a substituted or unsubstituted $C_8$-$C_{18}$ cycloalkynyl group, a substituted or unsubstituted $C_5$-$C_{18}$ heteroalkyl group, a substituted or unsubstituted $C_5$-$C_{18}$ heterocycloalkyl group, a substituted or unsubstituted $C_7$-$C_{30}$ arylalkyl group, a substituted or unsubstituted $C_7$-$C_{30}$ aryloxyalkyl group, or a substituted or unsubstituted $C_7$-$C_{30}$ arylthioalkyl group.

In a specific aspect, R is a substituted or unsubstituted $C_5$-$C_{18}$ alkyl group, a substituted or unsubstituted $C_5$-$C_{18}$ alkenyl group, or a substituted or unsubstituted $C_5$-$C_{18}$ alkynyl group. In one aspect, R is substituted with one or more $C_1$-$C_{20}$ alkyl groups, $C_6$-$C_{20}$ aryl, and/or $C_7$-$C_{13}$ arylalkyl groups. In another aspect, R is substituted with one or more $C_1$-$C_4$ alkyl groups or a $C_6$-$C_{10}$ aryl group.

In a more specific aspect, R is a linear, substituted or unsubstituted $C_5$-$C_{18}$ alkyl group.

The term "substituted", as used herein, means that any one or more hydrogens on the designated atom or group is replaced with a group at least one group selected from a halide (F—, Cl—, Br—, I—), a hydroxyl, a $C_1$ to $C_{20}$ alkoxy, a cyano, a $C_1$ to $C_{20}$ alkyl, a $C_2$ to $C_{16}$ alkenyl, a $C_2$ to $C_{16}$ alkynyl, a $C_6$ to $C_{20}$ aryl, a $C_7$ to $C_{13}$ arylalkyl, a $C_7$ to $C_{13}$ aryloxyalkyl, a $C_7$ to $C_{13}$ arylthioalkyl, a $C_1$ to $C_{20}$ heteroalkyl, a $C_3$ to $C_{20}$ cycloalkyl, and a $C_5$ to $C_{15}$ heterocycloalkyl, provided that the designated atom's normal valence is not exceeded. When a substituent is oxo (i.e., =O), then 2 hydrogens on the carbon atom are replaced. When aromatic moieties are substituted by an oxo group, the aromatic ring is replaced by the corresponding partially unsaturated ring. For example a pyridyl group substituted by oxo is a pyridone. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation into an effective therapeutic agent.

In a specific aspect, R is a $C_4$-$C_{18}$ alkyl group substituted with one or more a $C_1$ to $C_{20}$ alkyl groups, $C_6$ to $C_{20}$ aryl, and/or $C_7$ to $C_{13}$ arylalkyl groups. In another aspect, R is a $C_4$-$C_{18}$ alkyl group substituted with one or more $C_1$ to $C_4$ alkyl groups or a $C_6$ to $C_{10}$ aryl group.

As used herein, the term "alkyl" indicates a branched or straight-chain saturated aliphatic hydrocarbon group, having the specified number of carbon atoms. Thus, the term $C_1$-$C_8$ alkyl as used herein includes alkyl groups having from 1 to about 8 carbon atoms. When $C_0$-$C_n$ alkyl is used herein in conjunction with another group, for example, phenyl $C_0$-$C_4$ alkyl, the indicated group, in this case phenyl, is either directly bound by a single covalent bond ($C_0$), or attached by an alkyl chain having the specified number of carbon atoms, in this case from 1 to about 2 carbon atoms. Examples of alkyl include, but are not limited to, methyl, ethyl, n-propyl, iso-propyl, n-butyl, t-butyl, n-pentyl, and sec-pentyl.

As used herein, the term "alkenyl" indicates a branched or straight-chain hydrocarbon group including at least one carbon-carbon double bond, and having the specified number of carbon atoms. Examples of alkenyl include, but are not limited to, ethenyl, propenyl, including 1-propenyl and 2-propenyl, and propanedienyl.

As used herein, the term "alkynyl" indicates a branched or straight-chain hydrocarbon group including at least one carbon-carbon triple bond, and having the specified number of carbon atoms. Examples of alkynyl include, but are not limited to, ethynyl and propynyl, including 1-propynyl and 2-propynyl.

As used herein, the term "aryl" indicates aromatic groups containing only carbon in the aromatic ring or rings. Such aromatic groups may be further substituted with carbon or non-carbon atoms or groups. Typical aryl groups contain 1 to 3 separate, fused, or pendant rings and from 6 to about 18 ring atoms, without heteroatoms as ring members. Where indicated aryl groups may be substituted. Such substitution may include fusion to a 5 to 7-membered saturated cyclic group that optionally contains 1 or 2 heteroatoms independently chosen from N, O, and S, to form, for example, a 3,4-methylenedioxy-phenyl group. Examples of aryl include, but are not limited to, phenyl, naphthyl, including 1-naphthyl and 2-naphthyl, and bi-phenyl.

As used herein, the term "arylalkyl" indicates an aryl group covalently linked to an alkyl group that is linked to a compound, and having the specified number of carbon atoms. Examples of arylalkyl include, but are not limited to, benzyl and phenethyl, including 1-phenethyl and 2-phenethyl.

As used herein, the term "aryloxyalkyl" indicates an aryl group covalently linked to an alkyl group via oxygen, and the alkyl group further linked to a compound, and having the specified number of carbon atoms. Examples of aryloxyalkyl include, but are not limited to, phenoxymethyl and phenoxyethyl, including 1-phenoxyethyl and 2-phenoxyethyl.

As used herein, the term "arylthioalkyl" indicates an aryl group covalently linked to an alkyl group via sulfur, and the alkyl group further linked to a compound, and having the specified number of carbon atoms. Examples of arylthioalkyl include, but are not limited to, phenylthiomethyl and phenylthioethyl, including 1-phenylthioethyl and 2-phenylthioethyl.

As used herein, the term "cycloalkyl" indicates a group including at least one saturated hydrocarbon ring, and having the specified number of carbon atoms. Examples of cycloalkyl include, but are not limited to, cyclopropyl, cyclopropylmethyl, cyclopropylethyl, cyclobutyl, cyclopentyl, or cyclohexyl. Cycloalkyl may include a bridged or caged saturated group such as norbornyl or adamantyl.

As used herein, the term "cycloalkenyl" indicates a group including at least one hydrocarbon ring and at least one carbon-carbon double bond in the ring, and having the specified number of carbon atoms. Examples of cycloalkenyl include, but are not limited to, cyclopentenyl, including 1-cyclopentenyl, 2-cyclopentenyl, and 3-cyclopentenyl.

As used herein, the term "cycloalkynyl" indicates a group including at least one hydrocarbon ring and at least one carbon-carbon triple bond in the ring, and having the specified number of carbon atoms. Examples of cycloalkynyl include, but are not limited to, cyclooctynyl, including 1-cyclooctynyl, 2-cyclooctynyl, 3-cyclooctynyl, and 4-cyclooctynyl.

As used herein, the term "heteroalkyl" indicates an alkyl group including at least one heteroatom covalently bonded to one or more carbon atoms of the alkyl group. Each heteroatom may each independently be chosen from nitrogen (N), oxygen (O), sulfur (S), and phosphorus (P). Examples of heteroalkyl include, but are not limited to, methoxymethyl and methylthiomethyl.

As used herein, the term "heterocycloalkyl" indicates a group including a saturated cyclic ring containing from 1 to about 5 heteroatoms chosen from nitrogen (N), oxygen (O), and sulfur (S), and phosphorus (P) with remaining ring atoms being carbon. Heterocycloalkyl groups may have from 3 to about 8 ring atoms, and more typically have from 5 to 7 ring atoms. A $C_2$-$C_7$ heterocycloalkyl group contains from 2 to about 7 carbon ring atoms and at least one ring atom chosen from nitrogen (N), oxygen (O), sulfur (S), and phosphorus (P). Examples of heterocycloalkyl groups include, but are not limited to, morpholinyl, piperazinyl, piperidinyl, and pyrrolidinyl groups.

A dash ("-") that is not between two letters or symbols is used to indicate a point of attachment for a substituent. For example, —COOH is attached through the carbon atom.

In certain situations, the compounds of Formula I or II may possess asymmetry so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, it should be understood that all of the optical isomers and mixtures thereof are encompassed. In addition, compounds with carbon-carbon double bonds may occur in Z- and E-forms, with all isomeric forms of the compounds being included in the present invention. In these situations, the single enantiomers, i.e., optically active forms, can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example a chiral LC or HPLC column.

"Pharmaceutically acceptable salts" includes derivatives of the disclosed compounds wherein the parent compound is modified by making an acid or base salt thereof, and further refers to pharmaceutically acceptable solvates of such compounds and such salts. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional salts and the quaternary ammonium salts of the parent compound formed, for example, from inorganic or organic acids. For example, conventional acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like. The pharmaceutically acceptable salts of can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable.

In one aspect, provided herein are methods of treating a subject in need of treatment for a bacterial infection, comprising administering to the individual an antimicrobial compound or composition as described herein. The bacteria can be actively growing or in the stationary phase. In one aspect, administration of an antimicrobial compound is topical administration. In another aspect, administration of an antimicrobial compound is systemic administration such as oral administration.

The bacteria causing the infection can be Gram-negative, Gram-positive, or bacteria that are neither Gram-negative nor Gram-positive. Gram-negative bacteria include *Escherichia coli, Pseudomonas aeruginosa, Candidatus liberibacter, Agrobacterium tumefaciens, Branhamella catarrhalis, Citrobacter diversus, Enterobacter aerogenes, Klebsiella pneumoniae, Proteus mirabilis, Salmonella typhimurium, Neisseria meningitidis, Serratia marcescens, Shigella sonnei, Shigella boydii, Neisseria gonorrhoeae, Acinetobacter baumannii, Salmonella enteriditis, Fusobacterium nucleatum, Veillonella parvula, Bacteroides forsythus, Actinobacillus actinomycetemcomitans, Aggregatibacter actinomycetemcomitans, Porphyromonas gingivalis, Helicobacter pylori, Francisella tularensis, Yersinia pestis, Vibrio cholera, Shigella boydii, Morganella morganii, Edwardsiella tarda, Campylobacter jejuni,* and *Haemophilus influenzae.* In another embodiment, the bacteria are Gram-positive bacteria. Gram-positive bacteria include species of *Bacillus, Listeria, Staphylococcus, Streptococcus, Enterococcus,*

*Corynebacterium, Propionibacterium* and *Clostridium*. Specific Gram-positive bacteria include *Staphylococcus aureus, Staphylococcus epidermidis, Enterococcus faecium, Enterococcus faecalis, Streptococcus pyogenes, Bacillus anthraces* and *Bacillus cereus*. In a specific embodiment, the bacteria are one or more drug resistant bacteria. Bacteria that are neither Gram-negative nor Gram-positive include *Borrelia burgdorferi, Mycobacterium leprae, Mycobacterium tuberculosis* and other Mycobacteria. Further included are bacteria such as *Chlamydia* and *Mycoplasma* that do not have a cell wall. In certain aspects, the bacteria are resistant bacteria such as carbapenam-resistant bacteria, methicillin-resistant *Staphylococcus aureus*, vanccomycin-resistant *Enterococci* or multi-drug resistant *Neisseria gonorrhoeae*.

In another aspect, a method of inhibiting bacterial growth comprises contacting the bacteria with an antimicrobial compound as described herein. The bacteria can be actively growing or in the stationary phase. Methods of inhibiting bacteria include methods useful for treatment of a subject (human or veterinary) and also include methods useful for inhibiting bacteria outside of a subject, such as use for sterilization and disinfection.

In one embodiment, the bacteria are in the form of a biofilm. A biofilm is a complex aggregate of microorganisms such as bacteria, wherein the cells adhere to each other on a surface. The cells in biofilms are physiologically distinct from planktonic cells of the same organism, which are single cells that can float or swim in liquid medium. Biofilms are involved in, for example, urinary tract infections, middle ear infections, dental plaques, gingivitis, coatings of contact lenses, cystic fibrosis, and infections of joint prostheses and heart valves.

The antimicrobial compounds and compositions may be administered prophylactically, chronically, or acutely. For example, such compounds may be administered prophylactically to patients known to be prone to bacterial infections, or who are known to have been exposed to potentially infectious agents. The compounds may also be administered prophylactically to patients suffering from other conditions, such as AIDS or other immune-system-suppressing conditions that render them susceptible to opportunistic infections. In addition to the prevention of such infections, chronic administration of the antimicrobial compounds will typically be indicated in treating refractory conditions, such as persistent infection by multiple drug-resistant strains of bacteria. Acute administration of the antimicrobial compounds is indicated to treat, for example, those subjects presenting with classical indications of bacterial infection.

As used herein, "contacting" means that a compound is provided such that it is capable of making physical contact with another element, such as a microorganism, a microbial culture or a substrate. In another embodiment, the term "contacting" means that the compound is introduced into a subject receiving treatment, and the compound is allowed to come in contact in vivo. Thus, contacting can include administration of a compound, that is, introducing the compound into the body, such as into the systemic circulation. Administration routes include but are not limited to, rectal, oral, buccal, sublingual, pulmonary, transdermal, transmucosal, as well as subcutaneous, intraperitoneal, intravenous, and intramuscular injection.

Since the antimicrobial compounds are antibacterially active and inhibit bacterial growth, they are also of use in treating bacterial contamination of a substrate, such as hospital instruments or work surfaces. In order to treat a contaminated substrate, the compounds may be applied to the site of such contamination in an amount sufficient to inhibit bacterial growth.

In certain embodiments, the compounds are administered to a patient or subject. A "patient" or "subject", used equivalently herein, means mammals and non-mammals. "Mammals" means a member of the class Mammalia including, but not limited to, humans, non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

The phrase "effective amount," as used herein, means an amount of an agent, which is sufficient enough to significantly and positively modify symptoms and/or conditions to be treated (e.g., provide a positive clinical response). The effective amount of an active ingredient for use in a pharmaceutical composition will vary with the particular condition being treated, the severity of the condition, the duration of the treatment, the nature of concurrent therapy, the particular active ingredient(s) being employed, the particular pharmaceutically-acceptable excipient(s)/carrier(s) utilized, and like factors within the knowledge and expertise of the attending physician. In general, the use of the minimum dosage that is sufficient to provide effective therapy is preferred. Patients may generally be monitored for therapeutic effectiveness using assays suitable for the condition being treated or prevented, which will be familiar to those of ordinary skill in the art.

The phrase "inhibitory amount", as used herein, means an amount of an agent (a compound or composition), which is sufficient to reduce the level or activity of bacterial infection to a statistically significant lesser value as compared to when the agent is not present.

The amount of compound effective for any indicated condition will, of course, vary with the individual subject being treated and is ultimately at the discretion of the medical or veterinary practitioner. The factors to be considered include the condition being treated, the route of administration, the nature of the formulation, the subject's body weight, surface area, age and general condition, and the particular compound to be administered. In general, a suitable effective dose is in the range of about 0.1 to about 500 mg/kg body weight per day, preferably in the range of about 5 to about 350 mg/kg per day. The total daily dose may be given as a single dose, multiple doses, e. g., two to six times per day, or by intravenous infusion for a selected duration. Dosages above or below the range cited above may be administered to the individual patient if desired and necessary.

Also included herein are pharmaceutical compositions comprising the antimicrobial compounds. As used herein, "pharmaceutical composition" means a therapeutically effective amount of the compound together with a pharmaceutically acceptable excipient, such as a diluent, preservative, solubilizer, emulsifier, adjuvant, and the like. As used herein "pharmaceutically acceptable excipients" are well known to those skilled in the art. In one aspect, a pharmaceutical composition is suitable for topical administration. In another aspect, a pharmaceutical composition is suitable for systemic administration.

Tablets and capsules for oral administration may be in unit dose form, and may contain excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulfate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavoring or coloring agents.

For topical application to the skin, the drug may be made up into a cream, lotion or ointment. Cream or ointment formulations that may be used for the drug are conventional formulations well known in the art. Topical administration includes transdermal formulations such as patches.

For topical application to the eye, the inhibitor may be made up into a solution or suspension in a suitable sterile aqueous or non-aqueous vehicle. Additives, for instance buffers such as sodium metabisulphite or disodium edeate; preservatives including bactericidal and fungicidal agents such as phenyl mercuric acetate or nitrate, benzalkonium chloride or chlorhexidine, and thickening agents such as hypromellose may also be included.

The active ingredient may also be administered parenterally in a sterile medium, either subcutaneously, or intravenously, or intramuscularly, or intrasternally, or by infusion techniques, in the form of sterile injectable aqueous or oleaginous suspensions. Depending on the vehicle and concentration used, the drug can either be suspended or dissolved in the vehicle. Advantageously, adjuvants such as a local anaesthetic, preservative and buffering agents can be dissolved in the vehicle.

Pharmaceutical compositions may conveniently be presented in unit dosage form and may be prepared by any of the methods well known in the art of pharmacy. The term "unit dosage" or "unit dose" means a predetermined amount of the active ingredient sufficient to be effective for treating an indicated activity or condition. Making each type of pharmaceutical composition includes the step of bringing the active compound into association with a carrier and one or more optional accessory ingredients. In general, the formulations are prepared by uniformly and intimately bringing the active compound into association with a liquid or solid carrier and then, if necessary, shaping the product into the desired unit dosage form.

The antimicrobial compounds may also be administered in combination with an additional active agent, such as, for example, an inhibitor of bacterial efflux. Efflux pumps are proteins that unidirectionally remove antibiotics from cytoplasmic compartments, and are considered to be a mechanism of antibacterial resistance. Bacterial efflux inhibitors include chalcone compounds as disclosed in WO 11/075136, the polybasic compounds disclosed in WO 10/054102, the quaternary alkyl ammonium functional compounds disclosed in WO 08/141012, the compounds disclosed in WO 05/007162, the substituted polyamines of WO 04/062674, which are incorporated herein by reference in their entirety.

In another embodiment, the antimicrobial compounds of Formula I can be administered with a second antibiotic. Exemplary second antibiotics include, for example, glycopeptides (e.g, vancomycin or teicoplanin); penicillins, such as amdinocillin, ampicillin, amoxicillin, azlocillin, bacampicillin, benzathine penicillin G, carbenicillin, cloxacillin, cyclacillin, dicloxacillin, methicillin, mezlocillin, nafcillin, oxacillin, penicillin G, penicillin V, piperacillin, and ticarcillin; cephalosporins, such as cefadroxil, cefazolin, cephalexin, cephalothin, cephapirin, cephradine, cefaclor, cefamandole, cefonicid, ceforanide, cefoxitin, and cefuroxime, cefoperazone, cefotaxime, cefotetan, ceftazidime, ceftizoxime, ceftriaxone, and moxalactam; carbapenems such as imipenem; monobactams such as aztreonam; tetracyclines such as demeclocycline, tigilcycline, doxycycline, methacycline, minocycline, and oxytetracycline; aminoglycosides such as amikacin, gentamicin, kanamycin, neomycin, netilmicin, paromomycin, spectinomycin, streptomycin, and tobramycin; polymyxins such as colistin, colistimathate, and polymyxin B, and erythromycins and lincomycins and also sulfonamides such as sulfacytine, sulfadiazine, sulfisoxazole, sulfamethoxazole, sulfamethizole, and sulfapyridine; trimethoprim, quinolones, novobiocin, pyrimethamine, rifampin, quinolines, fluoroquinolines; and combinations thereof.

The invention is further illustrated by the following non-limiting examples.

EXAMPLES

Materials and Methods

In Vivo Screen:

The high throughput screen for the anucleate cell assay was based on the assay described in Oyamada et al., "Anucleate Cell Blue Assay: A Useful Tool for Identifying Novel Type II Topoisomerase Inhibitors," Antimicrobial Agents and Chemotherapy, 50, pp. 348-350, (2006). Briefly, *E. coli* anucleate cell strain (SH3210; ΔtrpR5 his λ pXX747) is used in the assay. The plasmid pXX747 includes the repA gene under control of the $\lambda P_R$ promoter and LacZ gene. In nucleated cells, repressors supplied by the chromosomal cI gene of λ phage and lacI gene keep expression of repA and lacZ genes low. In anucleated cells, however, expression of repA is induced, causing plasmid amplification, and induction of lacZ expression. The anucleated cells thus appear fluorescent in the presence of a fluorescent substrate (e.g., DDOAG) for LacZ. The protocol is summarized as follows:

1. Prepare overnight culture of *E. coli* anucleate cell strain (SH3210) from LB-ampicillin plates.
2. Dilute starter culture 1:1000 with liquid LB treated with 50 mg/ml of ampicillin and incubate for approximately 2.5 hr at 37° C. until approximately 0.1 $OD_{600}$.
3. Split diluted culture into wells (200 μL)
   i. Positive control: 1 μL of 5.0 mM rifampicin (final 2×MIC=25 μM)
   ii. Negative control: 1 μL of DMSO
4. Incubate diluted culture with compounds for approximately 2.5 hr at 42° C. at 300 rpm in a clear plate.
5. Incubate cultures on ice for approximately 10 min until condensation on the cover disappears.
6. Measure absorbance at a wavelength of 595 nm.
7. In a black 96-well plate, add 80 μL of Z-buffer (600 mM $Na_2HPO_4$, 40 mM $NaH_2PO_4$, 10 mM KCl, 0.1 $MgSO_4$) to each well pre-loaded with the following reagents:

a. Cell lysis solution called Popculture™ (1:5 Popculture™ to buffer). Popculture™ is a buffered mixture of concentrated detergents.
b. 15 µM of 9H-(1,3-dichloro-9,9-dimethylacridine-2-one-7-yl) β-d-galactopyranoside (DDAOG) (3 µL of 5 mM DDAOG per 1 mL of buffer)
8. Transfer 20 µL of culture to wells containing Z-buffer.
9. Incubate covered at room temperature for 15 min.
10. Incubate plate at 37° C. for 20 min.
11. Add 50 µL of 1 M $Na_2CO_3$ to each well.
12. Shake for 30 s and measure fluorescence at a wavelength of 659 nm.
13. Normalize the fluorescence measurements by dividing by $OD_{595}$.

$$Beta\text{-}gal\ units^* = \frac{Fluorescence_{659}}{OD_{595}}$$

Bacterial Strains and Growth Conditions.

Organisms and strains used in this study and their genotypes are summarized in Table 2. Luria-Bertani (LB) media (10 g/L tryptone, 10 g/L NaCl, 5 g/L yeast extract, pH 7.0) was used to grow all bacterial strains, except *Streptococcus pyogenes*. *Streptococcus pyogenes* was grown in Mueller-Hinton broth containing 5% (v/v) sheep blood. All bacterial cultures were grown at 37° C. All the *E. coli* strains were grown while shaking at 200 rpm, while clinical pathogens were incubated without shaking.

micro-dilution method was utilized in 96-well clear flat-bottom plates (100 µL/well) according to the CLSI guidelines. All strains were grown at 37° C. for 16-18 hours in presence of various concentrations of compound. The MIC was determined by a visual inspection and experiments were performed in triplicate.

Calculation of the Minimum Bacterial Concentration (MBC).

The antibacterial mode (i.e., bactericidal, bacteriostatic) was determined by calculating the quotient of the MBC and the MIC. Compounds with a quotient >4 are defined as bacteriostatic; if the quotient is lower than 4, compounds are defined as bactericidal. A micro-dilution protocol was used to perform MIC and MBC experiments in triplicate according to the CLSI guidelines. MIC endpoints were determined by identifying the lowest concentration of antibiotic that completely inhibited growth by visual inspection. The total volume (100 µL) in the wells with no visual growth were plated on 1.5% (w/v) LB agar or 1.5% (w/v) Mueller-Hinton agar with 5% sheep blood and incubated for 22 hours at 37° C. The MBC was determined to be the lowest concentration of antibiotic that did not produce visible colonies.

Example 1: Selection of Compounds

Small molecule libraries at the UW-Madison Small Molecular Screening and Medicinal Chemistry Facility that included the Prestwick library of off-patent, FDA-approved

TABLE 2

List of Strains

| Organism/Strain | Genotype/Description |
| --- | --- |
| S. aureus FRI 100 | sea$^+$ (Tmm$^s$ Hem$^{+a}$ Em$^s$) |
| Streptococcus pyogenes | |
| E. coli BW25113 | Δ(araD-araB)567 ΔlacZ4787(::anB-3) lambda$^-$ rph-1 Δ(rhaD-rhaB)568 hsdR514 |
| E. coli BW25113 ΔtolC | BW25113 tolC::kan$^R$ |
| P. aeruginosa PAO1 | Prototroph |
| P. aeruginosa K1115 | ilv-220 thr-9001 leu-9001 met-9011 pur-67 aphA ΔmexCD-oprJ ΔmexAB-oprM |
| P. aeruginosa K1119 | PAO1 ΔmexAB-oprM |
| Salmonella typhimurium | Clinical isolates from the Department of Medical Microbiology and Immunology (MMI) at the University of Wisconsin-Madison |
| Vibrio cholerae | Clinical isolates from the Department of Medical Microbiology and Immunology (MMI) at the University of Wisconsin-Madison |
| Shigella boydii | Clinical isolates from the Department of Medical Microbiology and Immunology (MMI) at the University of Wisconsin-Madison |
| Morganella morganii | Clinical isolates from the Department of Medical Microbiology and Immunology (MMI) at the University of Wisconsin-Madison |
| Edwardsiella tarda | Clinical isolates from the Department of Medical Microbiology and Immunology (MMI) at the University of Wisconsin-Madison |
| Acinetobacter baumannii | Clinical isolates from the Department of Medical Microbiology and Immunology (MMI) at the University of Wisconsin-Madison |
| Enterobacter aerogenes | Clinical isolates from the Department of Medical Microbiology and Immunology (MMI) at the University of Wisconsin-Madison |
| Klebsiella pneumoniae | Clinical isolates from the Department of Medical Microbiology and Immunology (MMI) at the University of Wisconsin-Madison |

Determination of the Minimum Inhibitory Concentration (MIC) of Bacterial Growth.

The MIC of all the strains was determined in LB media except *Streptococcus pyogenes*, which was grown in Mueller-Hinton media containing 5% (v/v) sheep blood. The drugs and therapeutic compounds undergoing advanced toxicological evaluation in animal models were screened using the high throughput anucleate cell assay. 5-nonyloxytryptamine (Compound 1, Table 1) as a potent hit in this screen as it displayed a minimum inhibitory concentrations against *E. coli* BW25113 that was <100 µg/mL.

Compound 1 is known to be a serotonin receptor agonist; specifically, it targets the 5-HT1Dβ human homolog of the serotonin receptor family. Compound 1 was initially discovered in experiments designed to identify a serotonin agonist that binds 5-HT1Dβ receptors selectively without inhibiting 5-HT1A receptors. The selectivity of inhibition is critical as inhibition of the 5-HT1A receptors is believed to contribute to the side effects of the medically relevant serotonin agonist, sumatriptan. Sumatriptan displays 60-fold selectivity for 5-HT1Dβ receptors versus 5-HT1A receptors; Compound 1 binds the 5-HT1Dβ with 260-fold selectivity, which makes it a promising serotonin receptor agonist for cancer treatment.

Compound 1 was screened against a broad panel of human pathogens (Table 3). Compound 1 has an MIC of 3-12 μg/mL against the pathogens we tested; the only exception was *Pseudomonas aeruginosa* for which Compound 1 has an MIC of 24 μg/mL, which is consistent with the challenges of drug efflux in this organism.

TABLE 3

Minimum inhibitory concentration (MIC) and minimum bacterial concentration (MBC) of Compound 1 against various pathogenic bacterial strains

| Bacterial Strain | MBC (μg/mL) | MIC (μg/mL) | MBC/MIC | Antibacterial Mode |
|---|---|---|---|---|
| Pseudomonas aeruginosa | 96 | 24 | 4 | Bacteriostatic |
| Salmonella typhimurium | 24 | 6 | 4 | Bacteriostatic |
| Vibrio cholerae | 24 | 6 | 4 | Bacteriostatic |
| Shigella boydii | 6 | 6 | 1 | Bactericidal |
| Klebsiella pneumoniae | 6 | 6 | 1 | Bactericidal |
| Enterobacter aerogenes | >96 | 6 | >4 | Bacteriostatic |
| Acinetobacter baumannii | 6 | 6 | 1 | Bactericidal |
| Edwardsiella tarda | 12 | 6 | 2 | Bactericidal |
| Morganella morganii | 24 | 12 | 2 | Bactericidal |
| Staphylococcus aureus | 6 | 3 | 2 | Bactericidal |
| Streptococcus pyogenes | 24 | 24 | 1 | Bactericidal |

Example 2: Synthesis of Compound 1 and its Analogs 5-nonyloxytryptamine was synthesized according to methods in the art, specifically the methods of Glennon et al., "Binding of O-Alkyl Derivatives of Serotonin at Human 5-HT1Dβ Receptors," J. Med Chem, 39, pp. 314-322, (1996).

N-Boc-Serotonin:

In a round bottom flask, potassium carbonate (1.5 equiv.) was added in one portion to a suspension of serotonin HCl (1 equiv.) in $H_2O$. Once fully dissolved, di-tert-butyl dicarbonate (1 equiv.) was added via syringe and the mixture was stirred at 25° C. for 24 hours. The reaction mixture was diluted with $H_2O$ and the product was extracted three times with EtOAc. The combined EtOAc layers were washed with $H_2O$, 5% HCl and brine. The EtOAc portion was dried with $Mg_2SO_4$ and evaporated to yield a green/brown oil.

n-Boc-5-Alkyoxytryptamine:

In a round bottom flask, potassium carbonate (1.78 equiv.) was added to a solution of N-Boc-serotonin (1 equiv.) in acetonitrile. To the reaction suspension, bromoalkane (1 equiv.) was added via syringe and the reaction mixture was stirred under argon at 25° C. for 24 hours. After the reaction mixture cooled to room temperature, the solid was removed by vacuum filtration and the solvent was evaporated under reduced pressure. The crude product was purified using flash chromatography with silica gel and 25% EtOAc/Hexane as the mobile phase to yield N-Boc-5-alkyoxytryptamine as a yellow oil.

5-Alkyoxytryptamine:

A solution of HCl (3M) in EtOAc was added to a solution of N-boc-5-alkyoxytryptamine in EtOAc and the reaction mixture was stirred vigorously at 25° C. for 2 hours. The solvent was evaporated under reduced pressure and the crude product was washed with anhydrous diethyl ether. The solid product was collected by vacuum filtration, washed three times with anhydrous diethylether and once with EtOAc to yield the HCl salt of 5-alkyoxytryptamine.

Example 3: Measurement of Minimum Inhibitory Concentrations for Compound 1 and its Analogs Several analogs of Compound 1 (Compounds 7-12, Table 1) in which the alkyl group at the 5-hydroxy position of tryptamine and several structurally related compounds (Compounds 2-6, Table 1) were tested against the panel of pathogens (results are shown in Table 4). Comparison of the O-alkoxytryptamine analogs (Compounds 1 and 7-11) and other tryptamines (Compounds 2-6) demonstrate that the activity of Compounds 1 and 7-11 is unique to the O-alkoxytryptamine family of compounds. Compounds 2-6 include tryptamine (the scaffold for neurotransmitters) and commercially available analogs of serotonin, including: 5-methoxytryptamine (full agonist towards all 5-HT receptors except 5-HT3), 2-methyl-5-hydroxytryptamine (specific agonist activity at the 5-HT3 receptor), and 6-methoxytryptamine (an inactive agonist at the 5-HT receptors, but structurally related to the others). Compounds 2-6 were largely ineffective as antibiotics; data for Compounds 7-11 against *E. coli* is summarized in Table 5.

Compounds 10 and 11 displayed MICs that are either the same or 2× different from Compound 1, thereby suggesting that these compounds share the same potency.

TABLE 4

Minimum inhibitory concentrations (MIC) of analogs with various carbon chain lengths and substituents at the 5-hydroxy position of serotonin

| MIC (μg/mL) | Compound | | | | | | |
|---|---|---|---|---|---|---|---|
| Bacterial Strain | 1 | 7 | 8 | 9 | 10 | 11 | 12 |
| E. coli BW25113 | 6 | >74 | 42 | 6.3 | 13 | 14 | >124 |
| E. coli BW25113 ΔtolC | 1.5 | >74 | 42 | 3.2 | 3.2 | 1.8 | >124 |
| Psuedomonas aeruginosa | 24 | >74 | >83 | >101 | 25 | 56 | >124 |
| Salmonella typhimurium | 6 | >74 | 42 | 6.3 | 6.3 | 7 | >124 |
| Vibrio cholerae | 6 | >74 | 42 | 6.3 | 6.3 | 7 | >124 |
| Shigella boydii | 6 | >74 | 42 | 3.2 | 6.3 | 7 | >124 |
| Klebsiella pneumoniae | 6 | >74 | 42 | 6.3 | 13 | 7 | >124 |
| Enterobacter aerogenes | 6 | >74 | 42 | 13 | 13 | 14 | >124 |
| Acinetobacter baumannii | 6 | >74 | 42 | 6.3 | 13 | 7 | >124 |
| Edwardsiella tarda | 6 | >74 | 42 | 25 | 25 | 28 | >124 |
| Morganella morganii | 12 | >74 | >83 | >101 | >101 | >112 | >124 |
| Staphylococcus aureus | 3 | >74 | 42 | 6.3 | 6.3 | 3.5 | >124 |

TABLE 5

Minimum inhibitory concentration (MIC) of various serotonin analogs with structural modification other than the O-alkyl chain.

| MIC (µg/mL) | Compound Number | | | | |
|---|---|---|---|---|---|
| Bacterial Strain | 2 | 3 | 4 | 5 | 6 |
| E. coli BW25113 | >51 | >56 | >61 | >61 | >61 |
| E. coli BW25113 ΔtolC | >51 | >56 | >61 | >61 | >61 |

Based on the known biological activity of Compound 1, and without being held to theory, it was hypothesized that that these compounds may be most useful for treating pathogens topically. The activity of Compounds 1-3 and 7-11 against *Staphylococcus aureus* (3.0 µg/mL), *Pseudomonas aeruginosa* (24 µg/mL), and *Streptococcus pyogenes* (24 µg/mL) was tested. Utilizing Compound 1 as a topical therapeutic is attractive because bioavailability and toxicity have not yet been published for human clinical trials. For rodent studies, the current dosage of Compound 1 is $10^{-8}$ to $10^{-4}$ mmol/kg, which is approximately 0.1 µM. Comparing toxicological data of Compound 1 with the MIC measurements, topical application would be a suitable method of dosing. However, in another embodiment, dosing would be systemic.

Example 4: Measurement of Minimum Inhibitory Concentrations for Additional Analogs of Compound 1

Compounds 13, 14 and 15 were also tested in the bacterial MIC assay.

TABLE 6

Minimum inhibitory concentration (MIC) values of tryptamine analogs with modification of the primary amine against *E. coli* BW25113, *E. coli* BW25113 ΔtolC, *Bacillus subtilis* 168 and a panel of clinically isolated pathogens.

| MIC (µg/mL) | Compound | | |
|---|---|---|---|
| Bacterial Strain | 13 | 14 | 15 |
| E. coli BW25113 | >130 | >83 | 52 |
| E. coli BW25113 ΔtolC | >130 | >83 | 6.5 |
| Bacillus subtilis 168 | >130 | >83 | 52 |
| Psuedomonas aeruginosa | >130 | >83 | 52 |
| Salmonella typhimurium | >130 | >83 | 26 |
| Vibrio cholerae | >130 | >83 | >104 |
| Shigella boydii | >130 | >83 | 26 |
| Klebsiella pneumoniae | >130 | >83 | 26 |
| Enterobacter aerogenes | >130 | >83 | 52 |
| Acinetobacter baumannii | >130 | >83 | 52 |
| Edwardsiella tarda | >130 | >83 | 26 |
| Morganella morganii | >130 | >83 | >104 |
| Staphylococcus aureus | >130 | >83 | 6.5 |

Removing or protecting the primary amine on the tryptamine of Compound 1 abolished antibacterial activity, while replacement of the indole ring with a benzene ring maintained activity.

The activity of a phenyl (benzene ring replacement of indole ring in tryptamine) analog was also tested.

TABLE 7

Minimum inhibitory concentration (MIC) values of 1 and a phenyl (benzene ring replacement of indole ring in tryptamine) analog against *E. coli* BW25113, *E. coli* BW25113 ΔtolC and a panel of clinically isolated pathogens.

| MIC (µg/mL) | Compound | |
|---|---|---|
| Bacterial Strain | 1 | 16 |
| E. coli BW25113 | 20 | 5.3 |
| E. coli BW25113 ΔtolC | 5 | 2.6 |
| Psuedomonas aeruginosa | 24 | 21 |
| Salmonella typhimurium | 6.0 | 5.3 |
| Vibrio cholerae | 6.0 | 5.3 |
| Shigella boydii | 6.0 | 5.3 |
| Klebsiella pneumoniae | 6.0 | 5.3 |
| Enterobacter aerogenes | 6.0 | 5.3 |
| Acinetobacter baumannii | 6.0 | 5.3 |
| Edwardsiella tarda | 6.0 | 5.3 |
| Morganella morganii | 12 | 11 |
| Staphylococcus aureus | 3.0 | 5.3 |

Replacement of the indole ring with a benzene ring did not substantially diminish the antimicrobial activity.

In addition, the position and length of the ethylene moiety was changed.

TABLE 8

Minimum inhibitory concentration (MIC) values of 1 and phenyl analogs with position shift and length variation of the ethylene moiety.

| MIC (µg/mL) | Compound | | | | |
|---|---|---|---|---|---|
| Bacterial Strain | 1 | 16 | 17 | 18 | 19 |
| E. coli BW25113 | 6 | 5.3 | 5.3 | 9.4 | >40 |
| E. coli BW25113 ΔtolC | 1.5 | 2.6 | 1.3 | 4.7 | 10 |
| Bacillus subtilis | 0.76 | 0.66 | 0.66 | 4.7 | 40 |

Shortening the ethylene moiety impaired the antimicrobial activity of the compounds.

Example 5: Rabbit RBC Hemolysis Assay

Prior to preparing the RBCs, we serially diluted compound-containing PBS solutions into a 96-well plate (a final volume of 100 µL/well). A 0.25% Triton X solution was included as a positive control for hemolysis. For each assay, removed 1 mL of the RBC suspension was removed from the stock bottle and the cells were centrifuged for 2 min at 2000 rpm. Pelleted cells were resuspended in sterile PBS solution and centrifuged again. Washing was repeated three times. The cells were resuspended in PBS and diluted 5-fold into the same solution. 100 µL aliquots of RBCs were added into wells of a 96-well plate that contained an equal volume of a solution of compound in PBS. The plates were incubated for 6 or 17 hours at 37° C. During the incubation, un-lysed RBCs settled at the bottom of the wells. At the end of the incubation, 90 µL of the supernatant was transferred into the wells of a fresh 96-well plate, and measured the absorbance of the heme at $\lambda=405$ nm.

The results are shown in FIGS. 1A and B. For all 6 compounds tested, at concentrations higher than the MIC, hemolysis was high relative to the positive control (Triton X) for both the 6 hour and 17 hour treatment times. At the MIC and sub-MIC levels the hemolysis was lower, demonstrating some potential for toxicity improvement with synthetic development.

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

The invention claimed is:

1. A method of treating a subject in need of treatment for a bacterial infection comprising administering to the subject a compound of Formula III or IV, or a pharmaceutically acceptable salt thereof,

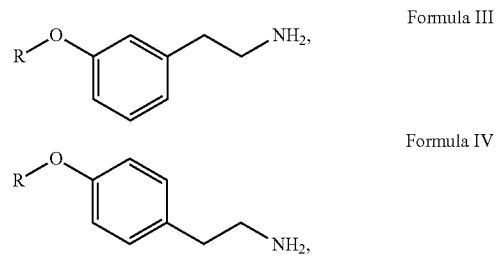

wherein R is a substituted or unsubstituted $C_5$-$C_{18}$ alkyl group, a substituted or unsubstituted $C_5$-$C_{18}$ alkenyl group, a substituted or unsubstituted $C_5$-$C_{18}$ alkynyl group, a substituted or unsubstituted $C_5$-$C_{18}$ cycloalkyl group, a substituted or unsubstituted $C_6$-$C_{18}$ cycloalkenyl group, or a substituted or unsubstituted $C_8$-$C_{18}$ cycloalkynyl group.

2. The method of claim 1, wherein, R is a substituted or unsubstituted $C_5$-$C_{18}$ alkyl group.

3. The method of claim 2, wherein R is substituted with one or more $C_1$-$C_{20}$ alkyl groups, $C_6$-$C_{20}$ aryl, and/or $C_7$-$C_{13}$ arylalkyl groups.

4. The method of claim 2, wherein R is substituted with one or more $C_1$-$C_4$ alkyl groups or a $C_6$-$C_{10}$ aryl group.

5. The method of claim 1, wherein the compound is

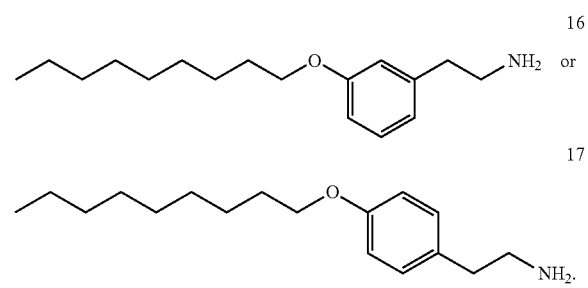

6. The method of claim 1, wherein the bacteria causing the infection are Gram-negative bacteria, Gram-positive bacteria, or bacteria that are neither Gram-positive nor Gram-negative.

7. The method of claim 6, wherein the Gram-negative bacteria is *Escherichia coli, Pseudomonas aeruginosa, Candidatus liberibacter, Agrobacterium tumefaciens, Branhamella catarrhalis, Citrobacter* di versus, *Enterobacter aerogenes, Klebsiella pneumoniae, Proteus mirabilis, Salmonella typhimurium, Neisseria meningitidis, Serratia marcescens, Shigella sonnei, Shigella boydii, Neisseria gonorrhoeae, Acinetobacter baumannii, Salmonella enteriditis, Fusobacterium nucleatum, Veillonella parvula, Bacteroides forsythus, Actinobacillus actinomycetemcomitans, Aggregatibacter actinomycetemcomitans, Porphyromonas gingivalis, Helicobacter pylori, Francisella tularensis, Yersinia pestis, Vibrio cholera, Shigella boydii, Morganella morganii, Edwardsiella tarda, Campylobacter jejuni,* or *Haemophilus influenzae.*

8. The method of claim 6, wherein the Gram-positive bacteria is a species of *Bacillus, Listeria, Staphylococcus, Streptococcus, Enterococcus, Corynebacterium, Propionibacterium* or *Clostridium.*

9. The method of claim 8, wherein the Gram-positive bacteria is *Staphylococcus aureus, Staphylococcus epidermidis, Enterococcus faecium, Enterococcus faecalis, Streptococcus pyogenes, Bacillus cereus,* or *Bacillus anthracis.*

10. The method of claim 9, wherein the bacteria are carbapenam-resistant bacteria, methicillin-resistant *Staphylococcus aureus*, vanccomycin-resistant *Enterococci* or multi-drug resistant *Neisseria gonorrhoeae.*

11. The method of claim 1, wherein the subject is a mammal.

12. The method of claim 11, wherein the mammal is a human.

13. The method of claim 1, wherein administration is topical administration.

14. The method of claim 1, wherein administration is systemic administration.

15. A method of inhibiting bacterial growth comprising contacting bacteria with an antimicrobially effective amount of a compound of Formula III or IV, or a pharmaceutically acceptable salt thereof,

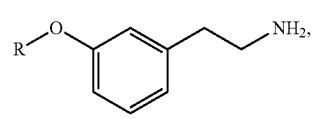

Formula III

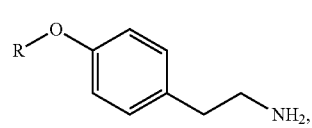

Formula IV wherein R is a substituted or unsubstituted $C_5$-$C_{18}$ alkyl group, a substituted or unsubstituted $C_5$-$C_{18}$ alkenyl group, a substituted or unsubstituted $C_5$-$C_{18}$ alkynyl groups substituted or unsubstituted $C_5$-$C_{18}$ cycloalkyl group, a substituted or unsubstituted $C_6$-$C_{18}$ cycloalkenyl group, or a substituted or unsubstituted $C_8$-$C_{18}$ cycloalkynyl group.

16. The method of claim 15, wherein the compound is

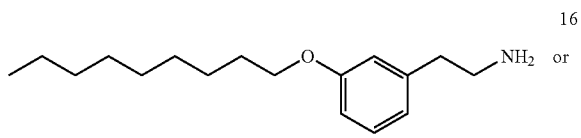

16

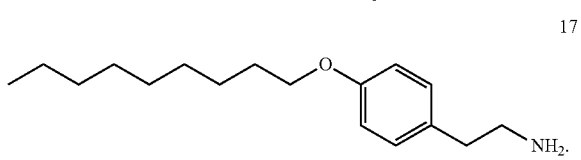

17

17. The method of claim 15, wherein the bacteria are actively growing or are in the stationary phase.

18. The method of claim 15, wherein the bacteria are in the form of a biofilm.

* * * * *